(12) United States Patent
Friedrichs

(10) Patent No.: US 7,319,524 B2
(45) Date of Patent: Jan. 15, 2008

(54) AIR PURGED OPTICAL DENSITOMETER

(75) Inventor: Hans P. Friedrichs, Tucson, AZ (US)

(73) Assignee: Honeywell International, Inc., Morristown, NJ (US)

( * ) Notice: Subject to any disclaimer, the term of this patent is extended or adjusted under 35 U.S.C. 154(b) by 348 days.

(21) Appl. No.: 11/092,471

(22) Filed: Mar. 28, 2005

(65) Prior Publication Data

US 2006/0215163 A1    Sep. 28, 2006

(51) Int. Cl.
*G01N 21/61* (2006.01)

(52) U.S. Cl. ............... 356/438; 356/435; 356/436

(58) Field of Classification Search ........ 356/432–439, 356/443, 446, 326; 250/343, 351–353, 228, 250/564, 573
See application file for complete search history.

(56) References Cited

U.S. PATENT DOCUMENTS

| | | | |
|---|---|---|---|
| 3,628,028 A | 12/1971 | Thorsheim | |
| 3,833,305 A | 9/1974 | Porter et al. | |
| 3,847,487 A | 11/1974 | Boll | |
| 3,862,568 A * | 1/1975 | Schlatter et al. | 73/32 A |
| 3,954,342 A | 5/1976 | Boeke | |
| 4,066,364 A | 1/1978 | Emerson | |
| 4,413,911 A * | 11/1983 | Rice et al. | 356/438 |
| 4,647,780 A * | 3/1987 | Dunkel | 250/573 |
| 4,651,004 A * | 3/1987 | Uno et al. | 250/343 |
| 4,787,750 A | 11/1988 | Nelson et al. | |
| 5,353,629 A | 10/1994 | Hunter | |
| 5,374,992 A | 12/1994 | Pye et al. | |
| 5,404,228 A | 4/1995 | McGowan | |
| 5,424,842 A | 6/1995 | Poorman | |
| 6,040,904 A * | 3/2000 | Fallet et al. | 356/236 |

FOREIGN PATENT DOCUMENTS

| | | |
|---|---|---|
| EP | 0539202 | 10/1992 |
| EP | 0762113 | 3/1997 |

OTHER PUBLICATIONS

PCT International Search, Jul. 2006.
Report PCT/US2006/010719, Jul. 20, 2006.

* cited by examiner

*Primary Examiner*—Sang H. Nguyen
(74) *Attorney, Agent, or Firm*—Ingrassia Fisher & Lorenz

(57) ABSTRACT

An advanced gas purged optical densitometer that significantly decreases the likelihood of optical component contamination and unstable optical path reduction includes an optical emitter, an optical receiver, and an optical path purge device. The optical emitter emits a light beam along an optical axis, through the optical purge path device and a test fluid. The optical receiver receives the light beam after it traverses the optical path purge device and the test fluid, and supplies a signal representative of intensity of the received light beam. The optical path purge device is configured to prevent contamination of the optical emitter and optical receiver, and to maintain a substantially optical path length of the test fluid.

18 Claims, 3 Drawing Sheets

AIR PURGED OPTICAL DENSITOMETER

TECHNICAL FIELD

The present invention relates to an optical densitometer and, more particularly, to an advanced gas purged optical densitometer that significantly decreases the likelihood of optical component contamination and unstable optical path reductions.

BACKGROUND

Various systems and devices have been devised to detect, and measure the density of, various fluids, including gas, as well as particulate that may be suspended within these various fluids. For example, many fire detection systems use densitometers to detect the presence of smoke within an environment. As is generally known, smoke is essentially fine particulates, such as carbon, that are generated by combustion and that are suspended in a gas, such as air. Smoke particulates are typically opaque, or at least reflective. Thus, various types of optical densitometers have been developed that detect the presence of smoke, and in some instances the density of smoke, in a gas by measuring the opacity or optical density of the gas.

One particular type of optical densitometer that has been developed includes an optical emitter and an optical receiver, spaced apart from one another in a measurement environment. The optical emitter is configured to emit a relatively constant intensity light beam. The optical receiver is configured to receive the emitted light beam and, upon its receipt, to generate a signal representative of the intensity of the received light beam. If smoke is present within the measurement environment between the optical emitter and optical receiver, the intensity of the emitted light beam may be attenuated before it is received by the optical receiver. Thus, the signal generated by the optical receiver may be representative of this reduction in received light beam intensity.

Although the above-described optical densitometer generally works well, it does suffer certain drawbacks. For instance, the particulate within the measurement environment may adhere to the optical emitter and optical receiver, which can significantly reduce the accuracy of the densitometer. Moreover, if not removed, the amount of particulate adhered to the optical emitter and optical receiver may build up over time, which may have a gradual, continual, yet unpredictable affect on densitometer accuracy.

To alleviate some of the concerns noted above, an optical densitometer configuration was developed in which a source of clean purge gas is used to prevent particulate adherence to the optical emitter and optical receiver. In such a configuration, sometimes referred to as a pinhole purge system, the optical emitter and optical receiver are each housed within individual instrument chambers, which are separated from one another by a measurement chamber. The instrument chambers each include an aperture through which the emitted light beam passes, and each is supplied with a flow of pressurizing air. Thus, the light beam emitted by the optical emitter passes through its instrument chamber aperture, into and through the measurement chamber, and through the aperture in the other instrument chamber, where it is received by the optical receiver. The measurement chamber includes the gas whose density is being measured. This gas is prevented from entering the instrument chambers because the flow of pressurizing air into the instrument chambers exits each instrument chamber via its aperture. Thus, particulate in the measurement chamber cannot adhere to the optical emitter or optical receiver.

Although the above-described pinhole purge system alleviates the problem of particulate adhering to the optical emitter and receiver, it too suffers certain drawbacks. For example, because the pressurized air flows out the instrument chamber apertures along the optical axis between the optical emitter and receiver, the effective optical path length between the emitter and receiver can be shortened, and reduce densitometer accuracy. Moreover, any variation if flow rate of the pressurized air through the instrument chamber apertures can cause variations in the effective optical path length. This latter factor, coupled with the inherent turbulence and swirling effects within the measurement chamber, can result in a relatively unstable effective optical path length, which can adversely affect overall accuracy.

Hence, there is a need for an optical densitometer that addresses one or more of the above-noted drawbacks. Namely, an optical densitometer that is not subject to particulate adhering to its optical instrumentation and/or that does not suffer from variations in effective optical path length and/or accuracy. The present invention addresses one or more of the drawbacks.

BRIEF SUMMARY

The present invention provides an advanced gas purged optical densitometer that significantly decreases the likelihood of optical component contamination and unstable optical path reductions.

In one embodiment, and by way of example only, an optical densitometer includes an optical emitter, an optical receiver, and an optical path purge device. The optical emitter is configured to emit a light beam, having an optical intensity, along an optical axis, the light beam. The optical receiver is spaced-apart from the optical emitter and is configured to receive at least a portion of the emitted light beam. The optical receiver is operable, upon receipt of the emitted light beam, to supply a signal representative of the optical intensity of the received light beam. The optical path purge device is positioned between the optical emitter and the optical receiver, and includes a first optical port, a second optical port, an optical passageway, a purge gas inlet port, a purge gas exhaust port, and a purge gas flow passage. The optical passageway extends between the first and second optical ports, and the first and second optical ports and the optical passageway are all disposed at least partially along the optical axis to thereby allow light beam transmission therethrough. The purge gas inlet port is adapted to receive a flow of purge gas. The purge gas flow passage extends between the purge gas inlet port and the purge gas outlet port, is in fluid communication with the optical passageway, and is disposed at least substantially transverse thereto. The purge gas flow passage is configured, upon the purge gas flowing therethrough, to create a differential pressure between the purge gas flow passage and the first and second optical ports that draws gas into the optical passageway via the first and second optical ports.

Other independent features and advantages of the preferred optical densitometer will become apparent from the following detailed description, taken in conjunction with the accompanying drawings which illustrate, by way of example, the principles of the invention.

DETAILED DESCRIPTION OF A PREFERRED EMBODIMENT

The following detailed description of the invention is merely exemplary in nature and is not intended to limit the invention or the application and uses of the invention. Furthermore, there is no intention to be bound by any theory presented in the preceding background of the invention or the following detailed description of the invention. In this regard, although the densitometer is described herein as being used to detect smoke, it will be appreciated that it can be used to detect any one of numerous other fluids or solids, and can also be used to determine the density of any one of numerous types of fluids, in both liquid and gaseous forms.

Figure 1:
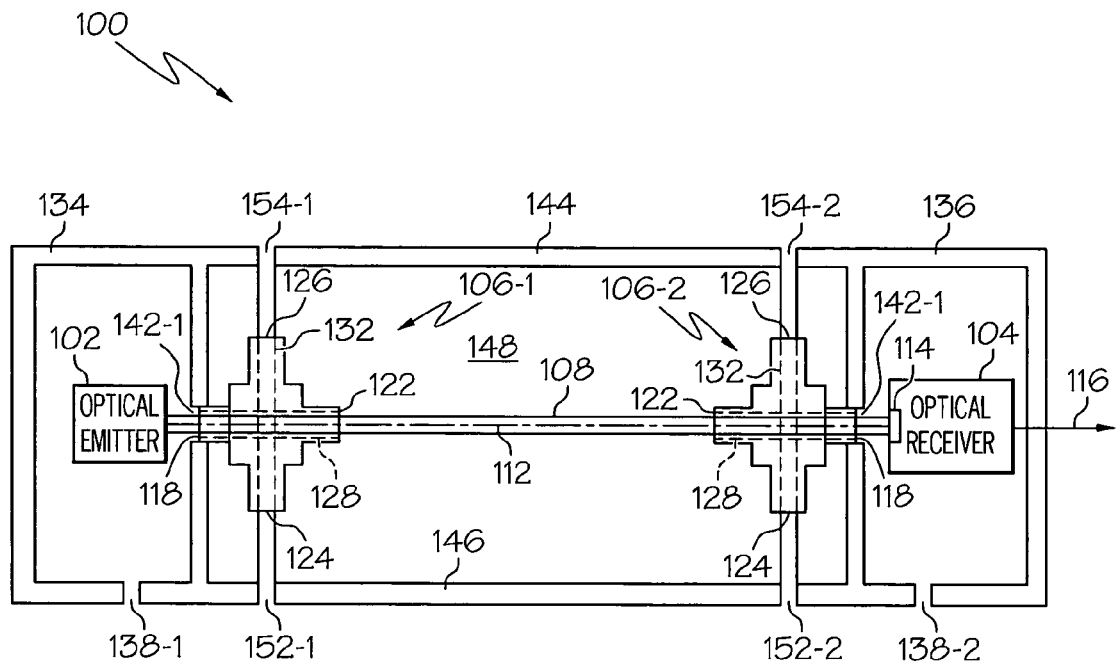
FIG. 1 is a schematic representation of an exemplary gas purged optical densitometer according to an embodiment of the present invention.

Turning now to the description, and with reference to FIG. 1, an exemplary gas purged optical densitometer is shown. The depicted densitometer 100 includes an optical emitter 102, an optical receiver 104, and a pair of optical path purge devices 106 (106-1, 106-2). The optical emitter 102, when appropriately energized, is configured to emit a light beam 108, preferably of a fixed optical intensity, along an optical axis 112. The optical emitter 102 may be implemented using any one of numerous devices now know or developed in the future that emit a beam of light. For example, the optical emitter 102 could be implemented using any one of numerous types of laser diodes. Though not depicted, it will be appreciated that the optical emitter 102 could additionally be implemented with one or more lenses and one or more filters to focus the emitted light beam 108 along the optical axis 112 and filter unwanted light from the emitted light beam 108, respectively.

The optical receiver 104 is spaced-apart from, and is disposed relative to, the optical emitter 102 such that it will receive at least a portion of the emitted light beam 108. The optical receiver 104 includes a light sensitive section 114, thus it is preferably disposed such that the light sensitive section 114 is positioned on the optical axis 112. The optical receiver 104 is operable, upon receipt of the emitted light beam 108 by the light sensitive section 114, to supply a signal 116 that is representative of the optical intensity of the received light beam. The optical receiver 104, similar to the optical emitter 102, may be implemented using any one of numerous devices now know or developed in the future that are responsive to the light beam 108 and supply a signal representative of the optical intensity of the received light beam. For example, the optical emitter 102 could be implemented using any one of numerous types of photodiodes. Moreover, and while also not being depicted, it will be appreciated that the optical emitter 102 could be implemented with one or more lenses and one or more filters to focus the received light beam 108 onto the light sensitive section 114 and filter unwanted light from the received light beam 108, respectively.

The optical path purge devices 106 are positioned between the optical emitter 102 and the optical receiver 104, and each includes a first optical port 118, a second optical port 122, a purge gas inlet port 124, and a purge gas exhaust port 126. The optical path purge devices 106 also each include an optical passageway 128 and a purge gas flow passage 132, both of which are shown in phantom in FIG. 1. The optical passageway 128 extends between the first and second optical ports 118, 122, and the first and second optical ports 118, 122 and the optical passageway 128 are all disposed at least partially along the optical axis 112. Thus, the emitted light beam 108 is transmitted through each of the optical passageways 128.

The purge gas flow passage 132 extends between the purge gas inlet port 124 and the purge gas exhaust port 126. As FIG. 1 also shows, the purge gas flow passage 132 is in fluid communication with, and is disposed at least substantially transverse to, the optical passageway 128. The optical path purge device purge gas inlet ports 124 are each adapted to receive a flow of purge gas. It will be appreciated that the purge gas may be any one of numerous types of suitable gases, and may be supplied from any one of numerous suitable sources. For example, in the depicted embodiment, the purge gas is compressed air that is supplied from a non-illustrated compressed air source.

The purge gas flow passage 132 is configured, upon the purge gas flowing through it, to create a differential pressure between the purge gas flow passage 132 and the first and second optical ports 118, 122. The differential pressure that is created draws gas into the optical passageway 128 via the first and second optical ports 118, 122. A more detailed description of the construction of the optical path purge devices 106, which provides this functionality, will be described further below. Before doing so however, the reminder of the densitometer 100 depicted in FIG. 1 will first be described.

As FIG. 1 shows, the optical emitter 102 and optical receiver 104 are each preferably disposed, at least partially, within separate chambers. More specifically, the optical emitter 102 is disposed within an emitter chamber 134 and the optical receiver 104 is disposed within a receiver chamber 136. The emitter chamber 134 and the receiver chamber 136 enclose, or at least partially enclose, the optical emitter 102 and optical receiver 104, respectively, and each includes a fluid inlet port 138-1, 138-2 and a fluid outlet port 142-1, 142-2. The emitter and receiver chamber fluid inlet ports 138-1, 138-2 are each adapted to receive a flow of relief gas, and the emitter and receiver chamber fluid outlet ports 142-1, 142-2 are each coupled to, and are in fluid communication with, one of the optical path purge device first optical ports 118. The relief gas may be any one of numerous types of suitable gases and may be supplied from any one of numerous suitable sources. For example, in the depicted embodiment the relief gas is air that is supplied to the emitter and receiver chambers 134, 136 from a non-illustrated fresh air source.

The emitter chamber 134 and the receiver chamber 136 are separated from one another via an environmental chamber 144. The environmental chamber 144 encloses, or at least partially encloses, each of the optical path purge devices 106, and includes an inner surface 146 that defines a test volume 148 in which the test fluid whose density is to be measured is introduced. As was noted above, the densitometer 100 may be used to measure the density of any one of numerous types of fluids, including both gas and liquid, but in the preferred embodiment the test fluid is a gas, and more preferably is air. Moreover, the densitometer 100, though not so limited, is preferably configured to detect the presence of smoke within the air that is introduced into the test volume 148. It will be appreciated that the test fluid may be introduced into the test volume 148 in any one of numerous, non-illustrated manners. For example, the test fluid may be supplied to the test volume 148 via a sample pump that draws fluid from a particular test environment, or it may simply be disposed within and vented to the particular test environment of interest.

No matter the specific manner in which the test fluid is introduced to the test volume 148, it is seen in FIG. 1 that the environmental chamber 144 additionally includes a pair of purge gas inlet ports 152 (152-1, 152-2), and a pair of purge gas outlet ports 154 (154-1, 154-2). The purge gas inlet ports 152 are each in fluid communication with one of the optical path purge device purge gas inlet ports 124 and are each adapted to receive the flow of purge gas. Thus, when the purge gas is supplied to the environmental chamber purge gas inlet ports 152, the purge gas flows into the optical path purge device purge gas inlet ports 124, through the optical path purge device purge gas flow passages 132, out the optical path purge device purge gas exhaust port 126, and out the environmental chamber purge gas outlet ports 154.

Figure 2:
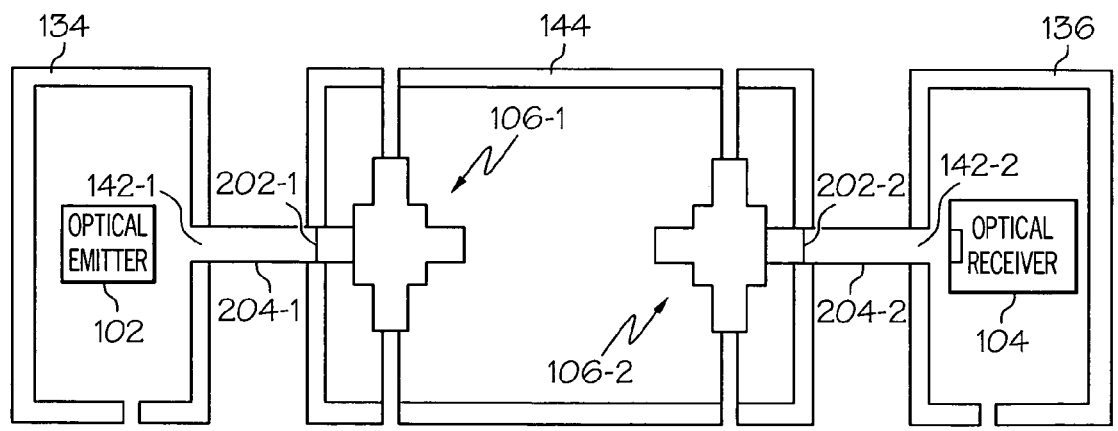
FIG. 2 is a schematic representation, similar to that of FIG. 1, depicting an exemplary gas purged optical densitometer according to an exemplary alternative embodiment of the present invention.

In the depicted embodiment, the optical path purge devices 106 are disposed within the environmental chamber 144. More specifically, the optical purge devices 106 are mounted within the environmental chamber 144 such that the optical path purge device first optical ports 118 are in fluid communication with one of the emitter chamber and receiver chamber fluid outlet port 142-1, 142-2, and the optical path purge device second optical ports 122 are each in fluid communication with the environmental chamber test volume 148. Although the optical path purge device inlet ports 118 are, in the depicted embodiment, mounted within the emitter chamber and receiver chamber fluid outlet ports 142-1, 142-2, it will be appreciated that this is merely exemplary. In an exemplary alternative embodiment, which is shown in FIG. 2, the environmental chamber 144 includes a pair of relief gas inlet ports 202-1, 202-2 that are fluidly coupled to the emitter chamber and the receiver chamber fluid outlet ports 142-1, 142-2, respectively, via a pair of conduits 204-1, 204-2, respectively. In this exemplary alternative embodiment, the optical path purge device inlet ports 118 are mounted within, or otherwise fluidly coupled to, the environmental chamber relief gas inlet ports 202-1, 202-2.

Figure 3:
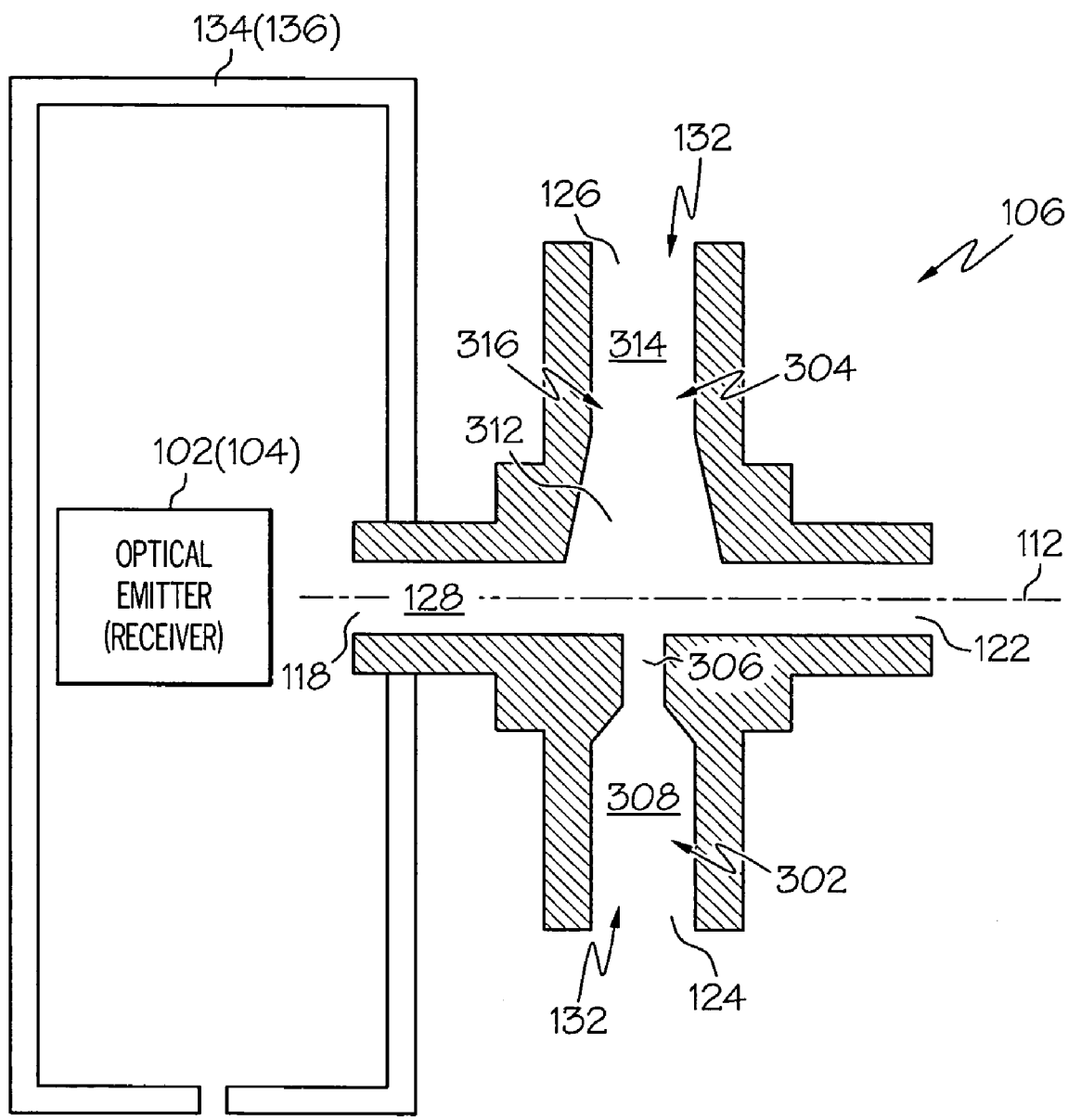
FIG. 3 is a simplified, close-up view, of a portion of the exemplary densitometers of FIGS. 1 and 2.

As was previously noted, the optical path purge device purge gas flow passage 132 is configured, upon purge gas flowing through it, to create a differential pressure between the purge gas flow passage 132 and the first and second optical ports 118, 122. It was also previously noted that this differential pressure draws gas into the optical passageway 128 via the first and second optical ports 118, 122. With reference now to FIG. 3, a more detail description of the optical path purge devices 106 will be described.

A cross section view of one of the optical path purge devices 106 is shown in FIG. 3, and clearly depicts the first and second optical ports 118, 122, the optical passageway 128, the purge gas inlet port 124, and the purge gas exhaust port 126. The depicted view also shows the purge gas flow passage 132 in greater detail in FIG. 3, which is shown to include a purge gas inlet section 302 and a purge gas outlet section 304. The purge gas inlet section 302 includes the purge gas inlet port 124, an inlet section outlet port 306, and an inlet section flow passage 308 that extends between the purge gas inlet port 124 and the inlet section outlet port 306. The inlet section flow passage 308 is configured to increase the fluid velocity of the purge gas flow. To do so, at least in the depicted embodiment, the inlet section flow passage 308 narrows from a first cross sectional flow area to a second, smaller cross sectional flow area. In this embodiment, the purge gas inlet port 124 also preferably has the first cross sectional flow area, and the inlet section outlet port 306 has the second, smaller cross sectional flow area.

The inlet section outlet port 306 fluidly communicates the inlet section flow passage 308 with the optical passageway 128. Thus, the purge gas that is directed into the purge gas inlet port 124 flows through the inlet section flow passage 308, where its fluid velocity is increased. The increased fluid velocity purge gas is then directed out the inlet section outlet port 306 and into the optical passageway 128. The inlet section outlet port 306 is preferably disposed relative to the optical passageway 128 such that the increased fluid velocity purge gas exits the inlet section 302 in a direction that is substantially transverse to the optical axis 112. Most preferably, the inlet section outlet port 306 is disposed such that increased fluid velocity purge gas exits the inlet section 302 substantially perpendicular to the optical axis 112.

Turning now to the purge gas flow passage exhaust section 304, it is seen that this section includes an inlet port 312, the purge gas exhaust port 126, and an exhaust flow passage 314. The exhaust section inlet port 312 is in fluid communication with the optical passageway 128 and is preferably positioned to receive at least a portion of the increased fluid velocity purge gas that exits the inlet section outlet port 306. Most preferably, and as shown in FIG. 3, the exhaust section inlet port 312 is centrally disposed directly opposite the inlet section outlet port 306. In any case, the exhaust section inlet port 312 is positioned such that the increased fluid velocity purge gas that flows through it is directed into and through the exhaust flow passage 314.

As may be seen in FIG. 3, a portion of the exhaust flow passage 314 and the exhaust section inlet port 312 preferably form a venturi throat 316. In particular, similar to the inlet section flow passage 308, the exhaust flow passage 314 narrows from a first cross sectional flow area, which is the same cross sectional flow area as the exhaust section inlet port 312, to a second cross sectional flow area, which is the same cross sectional flow area as the purge gas exhaust port 126, and that is smaller than the first cross sectional flow area. It will be appreciated that the transition between the first and section cross sectional flow. areas in the exhaust section 304 is more gradual than in the inlet section 302, and that the ratio of the first cross sectional flow area to the section cross sectional flow area is preferably larger in the inlet section 302 than it is in the exhaust section 304.

As is generally known, when a fluid flows through a venturi throat, such as the the venturi throat 316 in the exhaust section 304, the pressure at the inlet to the venturi throat is reduced. Thus, as the increased fluid velocity from the inlet section 302 flows into and through the venturi throat 316, the pressure at the exhaust section inlet port 312 is reduced, thereby creating the differential pressure between the purge gas flow passage 132 and the first and second optical ports 118, 122.

Figure 4:
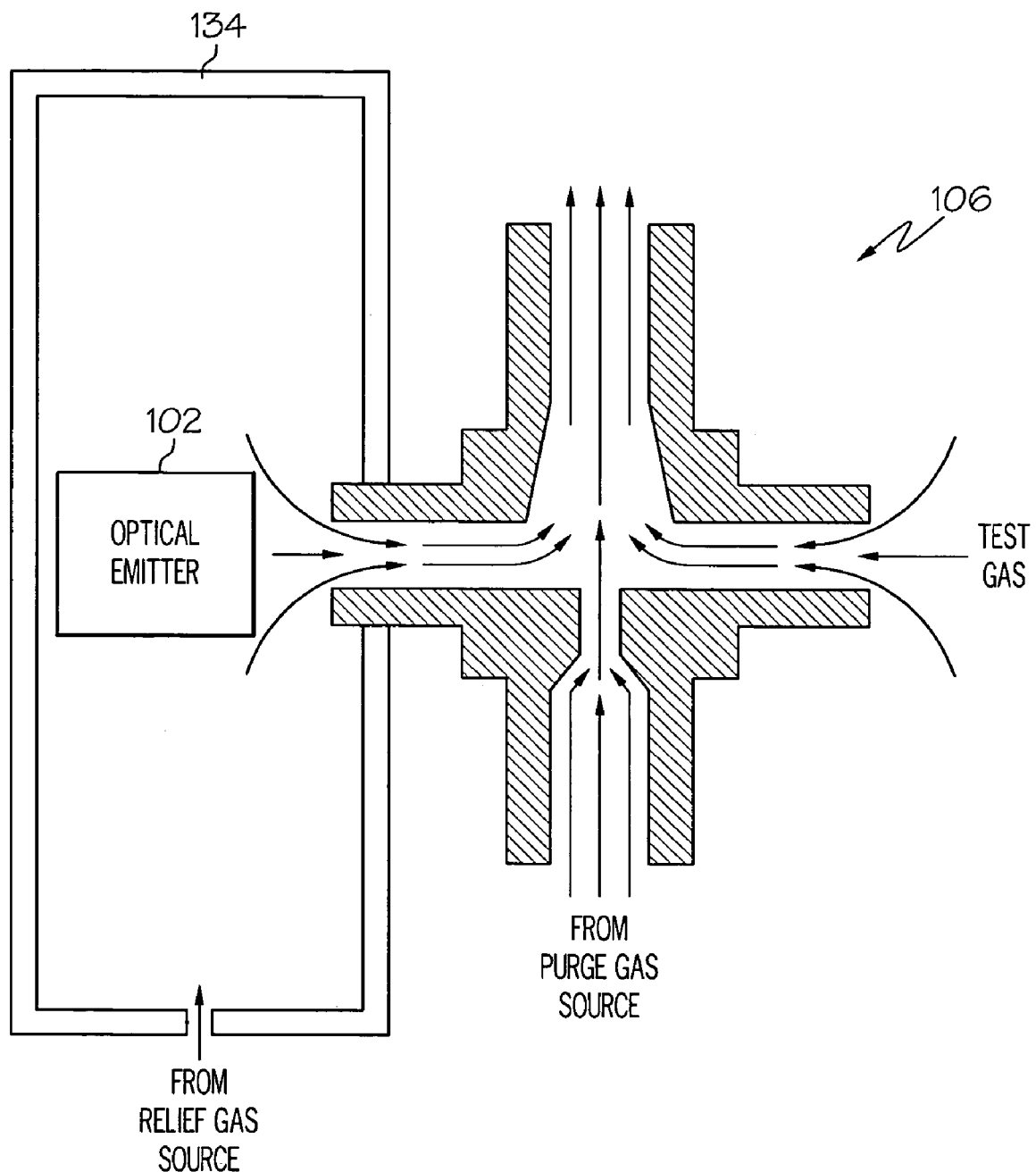
FIG. 4 is a simplified, close-up view, of a portion of the exemplary densitometers, similar to that shown in FIG. 3, and further illustrating the flow of various fluids therethrough.

Having described the densitometer 100 from a structural standpoint, with a brief overview of its functionality, a more detail description of the operation of the densitometer 100 and the various fluid flows into and through the optical path purge devices 106 will now be provided. In doing so, reference should be made to FIG. 4 and, as needed, in combination with FIGS. 1 and 3. Before proceeding with the description, it is noted that FIG. 4, similar to FIG. 3, depicts only one of the optical path purge devices 106 and, more specifically, the optical path purge device 106-1 that is fluidly coupled to the emitter chamber 134. It will nonetheless be appreciated that the other optical path purge device 106-2 functions identically.

During densitometer 100 operation, the optical emitter 102 is emitting the light beam 108, which passes through the optical path purge device optical passageways 128, and is received by the optical receiver 104. In addition, purge gas is being supplied to the optical purge device purge gas inlet ports 124, and relief gas is being supplied to the emitter and receiver chambers 134, 136. As the purge gas flows through the inlet section flow passages 308, the flow is restricted due to the reduction in cross sectional flow area, which in turn increases the fluid velocity of the purge gas. The increased fluid velocity purge gas flows transversely across the optical path purge device optical passageways 128, and into and through the purge gas flow passage exhaust sections 304.

In the purge gas flow passage exhaust sections 304, as the purge gas flows through the venturi throats 316 the pressure at the exhaust section inlet ports 312 decreases and creates a differential pressure between purge gas flow passages 132 and the first and second optical ports 118, 122. As a result, relief gas is drawn out of the emitter and receiver chambers 134, 136, into the first optical ports 118, and then partially through the optical passageways 128. The increased fluid velocity purge gas, coupled with the reduced pressure at the exhaust section inlet ports 306, then draws the relief fluid into and through the optical path purge device exhaust sections 304. The relief gas that is drawn out of the emitter and receiver chambers 134, 136 is replaced with relief fluid from the non-illustrated relief gas source. Thus, the emitter and receiver chambers 134, 136 are continuously replenished with clean, fresh relief gas.

In addition to drawing in relief fluid, the differential pressure draws the test fluid in the environmental chamber test volume 148 into the second optical ports 122. If particulate, such as smoke, is suspended in the test fluid, this too is drawn into the second optical ports 122. Thereafter, the test fluid flows partially through the optical passageways 128, where the increased fluid velocity purge gas, coupled with the reduced pressure at the exhaust section inlet ports 306, similarly draws the test fluid into and through the optical path purge device exhaust sections 304.

The densitometer configuration depicted and described herein allows the light beam 108 to be transmitted, uninterrupted between the optical emitter 102 and the optical receiver 104, while at the same time preventing contamination of the optical emitter 102 and optical receiver 104, and maintaining a substantially uniform, stable optical path length. In particular, as was noted above, the flow of purge gas, relief gas, and test gas into and through the optical path purge devices 106 prevents the test gas from entering the emitter and receiver chambers 134, 136, and thus contaminating the optical emitter 102 and optical receiver 104. Moreover, the test gas flow into and through the optical path purge devices 106 assures that the optical path length of the test fluid in the optical passageways 128 is uniform and stable.

While the invention has been described with reference to a preferred embodiment, it will be understood by those skilled in the art that various changes may be made and equivalents may be substituted for elements thereof without departing from the scope of the invention. In addition, many modifications may be made to adapt to a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. An optical densitometer, comprising:
    an optical emitter configured to emit a light beam along an optical axis, the light beam having an optical intensity;
    an optical receiver spaced-apart from the optical emitter and configured to receive at least a portion of the emitted light beam, the optical receiver operable, upon receipt of the emitted light beam, to supply a signal representative of the optical intensity of the received light beam; and
    an optical path purge device positioned between the optical emitter and the optical receiver, the optical path purge device including:
        a first optical port, a second optical port, and an optical passageway extending therebetween, the first and second optical ports and the optical passageway all disposed at least partially along the optical axis to thereby allow light beam transmission therethrough,
        a purge gas inlet port, a purge gas exhaust port, and a purge gas flow passage extending therebetween, the purge gas inlet port adapted to receive a flow of purge gas having a first fluid velocity, the purge gas flow passage in fluid communication with the optical passageway and disposed at least substantially transverse thereto, the purge gas flow passage configured, upon the purge gas flowing therethrough, to create a differential pressure between the purge gas flow passage and the first and second optical ports that draws gas into the optical passageway via the first and second optical ports,
        a purge gas inlet section including the purge gas inlet port, a purge gas outlet port, and a purge gas flow passage extending therebetween, the purge gas flow passage configured to increase the fluid velocity of the purge gas flowing therethrough, the purge gas outlet port in fluid communication with the optical passageway and disposed relative thereto such that the increased fluid velocity purge gas exits therefrom substantially transverse to the optical axis, and
        an exhaust section including an inlet port, the purge gas exhaust port, and an exhaust flow passage extending therebetween, the inlet port in fluid communication with the optical passageway and disposed relative thereto such that at least a portion of the increased fluid velocity purge gas flows through the inlet port and into the exhaust flow passage, the inlet port and at least a portion of the exhaust flow passage forming a venturi throat, whereby the differential pressure is created upon increased fluid velocity purge gas flowing therethrough.

2. The densitometer of claim 1, further comprising:
    an emitter chamber at least partially enclosing the optical emitter and including at least a fluid inlet port and a fluid outlet port, the emitter chamber fluid inlet port adapted to receive a flow of relief gas, the emitter chamber fluid outlet port in fluid communication with the optical path purge device first optical port.

3. The densitometer of claim 1, further comprising:
    a receiver chamber at least partially enclosing the optical receiver and including at least a fluid inlet port and a fluid outlet port, the receiver chamber fluid inlet port adapted to receive a flow of relief gas, the receiver chamber fluid outlet port in fluid communication with the optical path purge device optical passageway, whereby the light beam passes through the receiver chamber fluid outlet port.

4. The densitometer of claim 1, further comprising:
an environmental chamber disposed between the optical emitter and the optical receiver, the environmental chamber including an inner surface that defines a volume in which a measurement gas is disposed, a purge gas inlet port, a first relief gas inlet port, and a second relief gas inlet port, the purge gas inlet port in fluid communication with the optical path purge device purge gas inlet port and adapted to receive the flow of purge gas, the first and second relief gas inlet ports in fluid communication with the optical path purge device optical passageway, whereby the light beam passes through the environmental passageway.

5. The densitometer of claim 1, further comprising:
a second optical path purge device positioned between the optical emitter and the optical receiver, the second optical path purge device including:
a first optical port, a second optical port, and an optical passageway extending therebetween along the optical axis, whereby the light beam passes through the optical passageway, and
a purge gas inlet port, a purge gas exhaust port, and a purge gas flow passage extending therebetween, the purge gas inlet port adapted to receive a flow of purge gas, the purge gas flow passage in fluid communication with the optical passageway and disposed substantially transverse thereto, the purge gas flow passage configured, upon the purge gas flowing therethrough, to create a differential pressure between the purge gas flow passage and the first and second optical ports.

6. The densitometer of claim 5, wherein the second optical path purge device further comprises:
a purge gas inlet section including the purge gas inlet port, a purge gas outlet port, and a purge gas flow passage extending therebetween, the purge gas flow passage configured to increase the fluid velocity of the purge gas flowing therethrough, the purge gas outlet port in fluid communication with the optical passageway and disposed relative thereto such that the increased fluid velocity purge gas exits therefrom substantially transverse to the optical axis; and
an exhaust section including an inlet port, the purge gas exhaust port, and an exhaust flow passage extending therebetween, the inlet port in fluid communication with the optical passageway and disposed relative thereto such that at least a portion of the increased fluid velocity purge gas flows through the inlet port and into the exhaust flow passage, the inlet port and at least a portion of the exhaust flow passage forming a venturi throat, whereby the differential pressure is created upon increased fluid velocity purge gas flowing therethrough.

7. The densitometer of claim 5, further comprising:
an emitter chamber at least partially enclosing the optical emitter and including at least a relief gas inlet port and a relief gas outlet port, the emitter chamber relief gas inlet port adapted to receive a flow of relief gas, the emitter chamber relief gas outlet port in fluid communication with the optical path purge device first optical port; and
a receiver chamber at least partially enclosing the optical receiver and including at least a relief gas inlet port and a relief gas outlet port, the receiver chamber relief gas inlet port adapted to receive a flow of relief gas, the receiver chamber relief gas outlet port in fluid communication with the second optical path purge device first optical port.

8. The densitometer of claim 7, wherein the differential pressure draws the flow of relief gas into the emitter and receiver chambers, and into the optical purge device first optical ports.

9. The densitometer of claim 7, further comprising:
an environmental chamber disposed between the emitter chamber and the receiver chamber and at least partially enclosing the optical purge devices, the environmental chamber including an inner surface that defines a volume in which a measurement gas is disposed, the environmental chamber further including first and second purge gas inlet ports, each purge gas inlet port in fluid communication with one of the optical path purge device purge gas inlet ports and adapted to receive the flow of purge gas at the first fluid velocity.

10. The densitometer of claim 9, wherein the environmental chamber further includes first and second purge gas outlet ports, each purge gas outlet port in fluid communication with one of the optical path purge device exhaust section exhaust ports.

11. The densitometer of claim 10, wherein the differential pressure draws:
(i) the flow of relief gas into the emitter and receiver chambers, and into the optical purge device first optical ports; and
(ii) a portion of the measurement gas into each of the optical purge device second optical ports.

12. An optical densitometer, comprising:
an optical emitter configured to emit a light beam along an optical axis, the light beam having an optical intensity;
an optical receiver spaced-apart from the optical emitter and configured to receive at least a portion of the emitted light beam, the optical receiver operable, upon receipt of the emitted light beam, to supply a signal representative of the optical intensity of the received light beam;
first and second optical path purge devices positioned between the optical emitter and the optical receiver, each optical path purge device including:
a first optical port, a second optical port, and an optical passageway extending therebetween, the first and second optical ports and the optical passageway all disposed at least partially along the optical axis to thereby allow light beam transmission therethrough,
a purge gas inlet port, a purge gas exhaust port, and a purge gas flow passage extending therebetween, the purge gas inlet port adapted to receive a flow of purge gas having a first fluid velocity, the purge gas flow passage in fluid communication with the optical passageway and disposed at least substantially transverse thereto, the purge gas flow passage configured, upon the purge gas flowing therethrough, to create a differential pressure between the purge gas flow passage and the first and second optical ports that draws gas into the optical passageway via the first and second optical ports,
a purge gas inlet section including the purge gas inlet port, a purge gas outlet port, and a purge gas flow passage extending therebetween, the purge gas flow passage configured to increase the fluid velocity of the purge gas flowing therethrough, the purge gas outlet port in fluid communication with the optical passageway and disposed relative thereto such that the increased fluid velocity purge gas exits therefrom substantially transverse to the optical axis, and an exhaust section including an inlet port, the purge gas exhaust port, and an exhaust flow passage extending therebetween, the inlet port in fluid communication with the optical passageway and disposed relative thereto such that at least a portion of the increased fluid velocity purge gas flows through the inlet port and into the exhaust flow passage, the inlet port and at least a portion of the exhaust flow passage forming a venturi throat, whereby the differential pressure is created upon increased fluid velocity purge gas flowing therethrough.

13. The densitometer of claim 12, further comprising:
an environmental chamber disposed between the emitter chamber and the receiver chamber and at least partially enclosing the optical purge devices, the environmental chamber including an inner surface that defines a volume in which a measurement gas is disposed, the environmental chamber further including first and second purge gas inlet ports, each purge gas inlet port in fluid communication with one of the optical path purge device purge gas inlet ports and adapted to receive the flow of purge gas.

14. The densitometer of claim 13, wherein the environmental chamber further includes first and second purge gas outlet ports, each purge gas outlet port in fluid communication with one of the optical path purge device purge gas exhaust ports.

15. The densitometer of claim 13, further comprising:
an emitter chamber at least partially enclosing the optical emitter and including at least a relief gas inlet port and a relief gas outlet port, the emitter chamber relief gas inlet port adapted to receive a flow of relief gas, the emitter chamber relief gas outlet port in fluid communication with the optical path purge device first optical port; and a receiver chamber at least partially enclosing the optical receiver and including at least a relief gas inlet port and a relief gas outlet port, the receiver chamber relief gas inlet port adapted to receive a flow of relief gas, the receiver chamber relief gas outlet port in fluid communication with the second optical path purge device first optical port.

16. The densitometer of claim 15, wherein the differential pressure draws:
(i) the flow of relief gas into the emitter and receiver chambers, and into the optical purge device first optical ports; and
(ii) a portion of the measurement gas into each of the optical purge device second optical ports.

17. An optical densitometer, comprising:
an optical emitter configured to emit a light beam along an optical axis, the light beam having an optical intensity;
an optical receiver spaced-apart from the optical emitter and configured to receive at least a portion of the emitted light beam, the optical receiver operable, upon receipt of the emitted light beam, to supply a signal representative of the optical intensity of the received light beam;

an emitter chamber at least partially enclosing the optical emitter and including at least a relief gas inlet port and a relief gas outlet port, the emitter chamber relief gas inlet port adapted to receive a flow of relief gas;

a receiver chamber at least partially enclosing the optical receiver and including at least a relief gas inlet port and a relief gas outlet port, the receiver chamber relief gas inlet port adapted to receive a flow of relief gas;

first and second optical path purge devices positioned between the emitter and receiver chambers, each optical path purge device including:
a first optical port, a second optical port, and an optical passageway extending therebetween, the first and second optical ports and the optical passageway all disposed at least partially along the optical axis to thereby allow light beam transmission therethrough, a purge gas inlet section including a purge gas inlet port, a purge gas outlet port, and a purge gas flow passage extending therebetween, the purge gas inlet port adapted to receive a flow of purge gas at a fluid velocity, the purge gas flow passage configured to increase the fluid velocity of the purge gas flowing therethrough, the purge gas outlet port in fluid communication with the optical passageway and disposed relative thereto such that the increased fluid velocity purge gas exits therefrom at least substantially transverse to the optical axis, and an exhaust section including an inlet port, an exhaust port, and an exhaust flow passage extending therebetween, the inlet port in fluid communication with the optical passageway and disposed relative thereto such that at least a portion of the increased fluid velocity purge gas flows through the inlet port and into the exhaust flow passage, the inlet port and at least a portion of the exhaust flow passage forming a venturi throat, whereby, upon the increased fluid velocity purge gas flowing therethrough, a differential pressure is created between the purge gas flow passage and the first and second optical ports.

18. The densitometer of claim 17, further comprising:
an environmental chamber disposed between the emitter chamber and the receiver chamber and at least partially enclosing the optical purge devices, the environmental chamber including:
an inner surface that defines a volume in which a measurement gas is disposed, first and second purge gas inlet ports, each purge gas inlet port in fluid communication with one of the optical path purge device purge gas inlet ports and adapted to receive the flow of purge gas at the first flow velocity, and first and second purge gas outlet ports, each purge gas outlet port in fluid communication with one of the optical path purge device exhaust section exhaust ports, wherein the differential pressure draws:
(i) the flow of relief gas into the emitter and receiver chambers, and into the optical purge device first optical ports; and
(ii) a portion of the measurement gas into each of the optical purge device second optical ports.

* * * * *